(12) United States Patent
Kudo et al.

(10) Patent No.: US 11,773,100 B2
(45) Date of Patent: Oct. 3, 2023

(54) BISMALEIMIDE COMPOUND AND PRODUCTION METHOD THEREOF

(71) Applicant: Shin-Etsu Chemical Co., Ltd., Tokyo (JP)

(72) Inventors: Yuki Kudo, Annaka (JP); Yoshihiro Tsutsumi, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 28 days.

(21) Appl. No.: 17/155,596

(22) Filed: Jan. 22, 2021

(65) Prior Publication Data

US 2021/0246142 A1 Aug. 12, 2021

(30) Foreign Application Priority Data

Feb. 7, 2020 (JP) .................................. 2020-019292

(51) Int. Cl.
| | | |
|---|---|---|
| C08L 71/12 | (2006.01) | |
| C07D 487/04 | (2006.01) | |
| C07D 519/00 | (2006.01) | |
| C07D 403/14 | (2006.01) | |
| C08G 73/12 | (2006.01) | |

(52) U.S. Cl.
CPC .................. *C07D 487/04* (2013.01)

(58) Field of Classification Search
CPC .. C07D 487/04; C07D 519/00; C07D 403/14; C08G 73/1042; C08G 73/12; C08L 79/085; C08L 71/12
See application file for complete search history.

(56) References Cited

U.S. PATENT DOCUMENTS

| | | |
|---|---|---|
| 2007/0264438 A1 | 11/2007 | Kawai |
| 2007/0295607 A1 | 12/2007 | Kawai |
| 2011/0120761 A1 | 5/2011 | Kawai |
| 2014/0102623 A1 | 4/2014 | Kawai et al. |
| 2018/0009195 A1 | 1/2018 | Takeuchi et al. |

FOREIGN PATENT DOCUMENTS

| | | |
|---|---|---|
| JP | JP 2007-254709 A | 10/2007 |
| JP | JP 2007-254710 A | 10/2007 |
| JP | JP 2011-132507 A | 7/2011 |
| JP | JP 2017-119361 A | 7/2017 |
| JP | JP 2019-104843 A | 6/2019 |
| JP | JP 2019-173010 A | 10/2019 |
| WO | WO 2016/114287 A1 | 7/2016 |
| WO | WO 2019/189467 A1 | 10/2019 |

OTHER PUBLICATIONS

RN2490481-92-8, registry database compound, Oct. 15, 2020.*
Japanese Office Action for Appl. No. 2020-0192292 dated Dec. 20, 2022 (w/ English translation).

* cited by examiner

*Primary Examiner* — Sun Jae Yoo
(74) *Attorney, Agent, or Firm* — Birch, Stewart, Kolasch & Birch, LLP

(57) ABSTRACT

Provided is a bismaleimide compound having a favorable compatibility with other resins and contributing to a higher Tg. The compound is represented by the following formula (1)

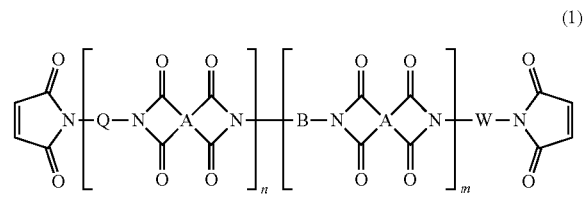

wherein A independently represents a tetravalent organic group having a cyclic structure, B independently represents a divalent hydrocarbon group having 6 to 200 carbon atoms, Q independently represents a cyclohexane backbone-containing divalent alicyclic hydrocarbon group having 6 to 60 carbon atoms, W represents B or Q, n represents 1 to 100, m represents 0 to 100, repeating units identified by n and m whose bonding pattern may be alternate, block or random are present in any order, and wherein Q is independently represented by the following formula (2):

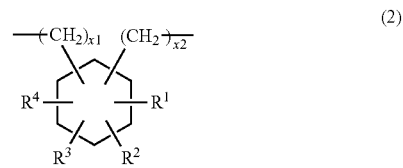

wherein each of $R^1$, $R^2$, $R^3$ and $R^4$ independently represents a hydrogen atom or an alkyl group having 1 to 5 carbon atoms, each of x1 and x2 represents a number of 0 to 4.

10 Claims, 1 Drawing Sheet

BISMALEIMIDE COMPOUND AND PRODUCTION METHOD THEREOF

BACKGROUND OF THE INVENTION

Field of the Invention

The present invention relates to a bismaleimide compound and a production method thereof.

Background Art

In recent years, as electronic devices are becoming smaller and reaching a higher level of performance, it is required that wirings in a multilayered printed-wiring board be established in a finer and highly dense manner. Further, since a material intended for use in high frequency ranges is required in the next generation, and a reduction in transmission loss is essential as a countermeasure for noises, an insulating material superior in dielectric properties needs to be developed.

As an insulating material for use in a multilayered printed-wiring board, there is known an epoxy resin composition(s) containing, for example, an epoxy resin, a particular phenolic curing agent, a phenoxy resin, rubber particles and a polyvinyl acetal resin, as are disclosed in JP-A-2007-254709 and JP-A-2007-254710. However, it has become clear that these materials are not satisfactory in terms of high-frequency application which is often referred to by the keyword "5G." In this regard, JP-A-2011-132507 reports that an epoxy resin composition comprising an epoxy resin, an active ester compound and a triazine-containing cresol novolac resin is effective in lowering a dielectric tangent. However, if used for high-frequency application, lower dielectric properties are required even with this type of material.

Meanwhile, WO 2016/114287 reports that a resin film made of a resin composition comprising a long-chain alkyl group-containing bismaleimide resin and a curing agent, as a non-epoxy material, is excellent in terms of exhibiting low dielectric properties. Since this composition is technically a combination of a long-chain alkyl group-containing bismaleimide resin and a hard low-molecular aromatic maleimide, a poor compatibility will be exhibited, property variation and curing unevenness will occur easily, and it is thus extremely difficult to reach a high glass-transition temperature (Tg) of 100° C. or higher as required for substrate use.

Further, researches in recent years have shown that there exists a trade-off correlation where due to the resin design of the above long-chain alkyl group-containing bismaleimide resin, poor dielectric properties will be exhibited if a higher Tg is sought, whereas a lower Tg will be exhibited if dielectric properties are to be improved. Furthermore, it has also been shown that if seeking a higher Tg, even identical long-chain alkyl group-containing bismaleimide resins themselves will undergo agglomeration and separation, and a compatibility between the resins will deteriorate as well.

In addition, disclosed in JP-A-2017-119361 and JP-A-2019-104843 are a polyimide(s) whose raw materials include an aromatic tetracarboxylic acid; a dimer diamine derived from a dimer acid as a dimer of an unsaturated fatty acid such as oleic acid; and an alicyclic diamine. However, this polyimide is unfit for use if hardened alone, and has a poor compatibility with other resins. Moreover, since the polyimide undergoes cyclodehydration at the time of hardening, swelling may occur under certain use conditions if, for example, the polyimide is used in the form of a layer being attached to a metallic foil.

SUMMARY OF THE INVENTION

Thus, it is an object of the present invention to provide a bismaleimide compound having a favorable compatibility with other resins, and contributing to a higher Tg.

The inventors of the present invention diligently conducted a series of studies to solve the abovementioned problems, and completed the invention as follows. That is, the inventors found that the following bismaleimide compound was capable of achieving the above object.

[1]
A bismaleimide compound represented by the following formula (1):

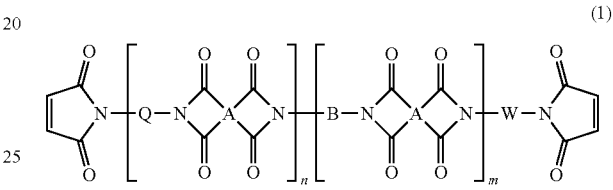

wherein A independently represents a tetravalent organic group having a cyclic structure, B independently represents a divalent hydrocarbon group having 6 to 200 carbon atoms, Q independently represents a cyclohexane backbone-containing divalent alicyclic hydrocarbon group having 6 to 60 carbon atoms, W represents B or Q, n represents 1 to 100, m represents 0 to 100, repeating units identified by n and m are present in any order, a bonding pattern of each of the repeating units n and m may be alternate, block or random, and
wherein Q is independently represented by the following formula (2):

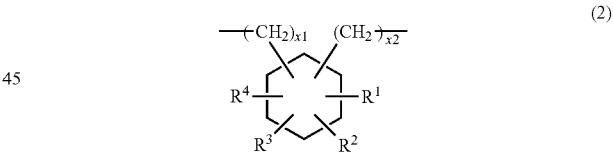

wherein each of $R^1$, $R^2$, $R^3$ and $R^4$ independently represents a hydrogen atom or an alkyl group having 1 to 5 carbon atoms, each of x1 and x2 represents a number of 0 to 4.

[2]
The bismaleimide compound according to [1], wherein A in the formula (1) represents any one of the tetravalent organic groups represented by the following structural formulae:

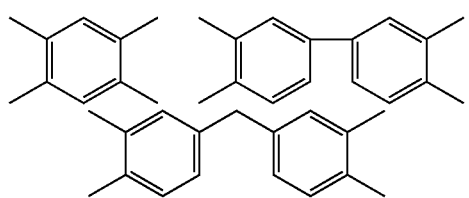

-continued

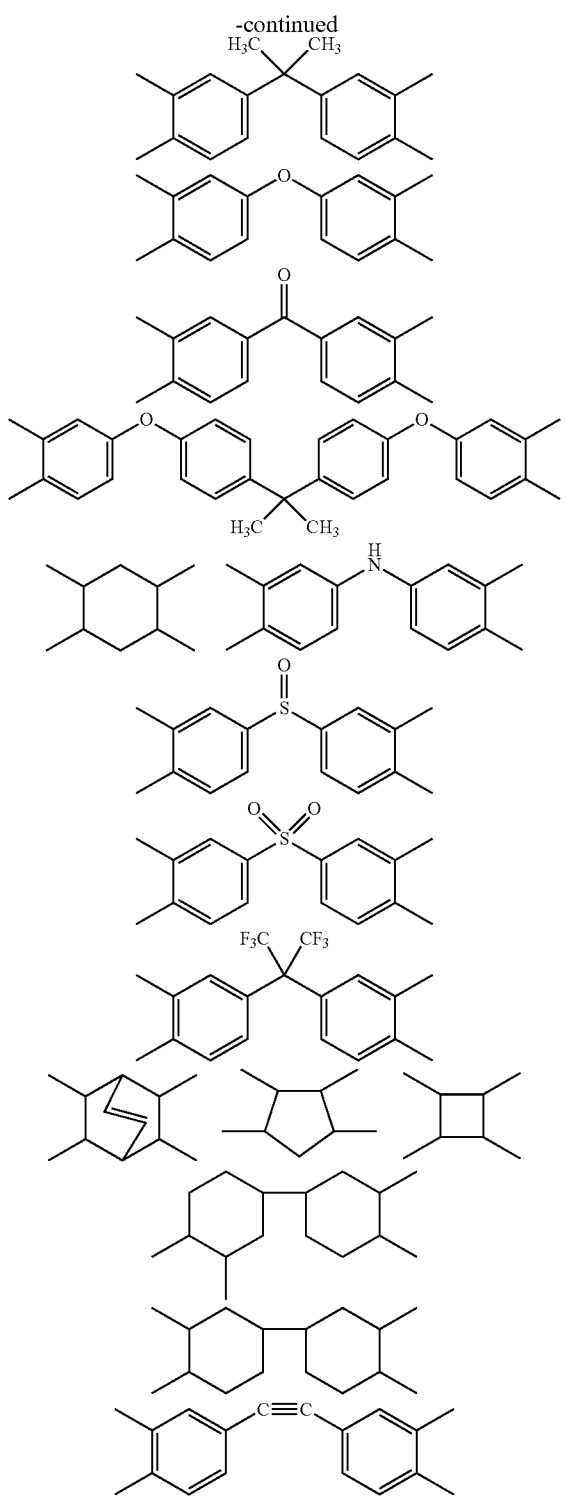

wherein bonds in the above structural formulae that are yet unbonded to substituent groups are to be bonded to carbonyl carbons forming cyclic imide structures in the formula (1).

[3]

The bismaleimide compound according to [1] or [2], wherein the bismaleimide compound represented by the formula (1) has a number average molecular weight of 3,000 to 50,000.

[4]

The bismaleimide compound according to any one of [1] to [3], wherein the bonding pattern of each of the repeating units identified by n and m is block in the bismaleimide compound represented by the formula (1).

[5]

The bismaleimide compound according to any one of [1] to [4], wherein B in the formula (1) comprises at least one of the divalent hydrocarbon groups represented by the following structural formulae (3-1) to (5):

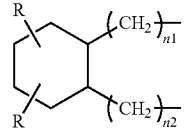

(3-1)

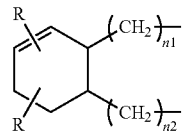

(3-2)

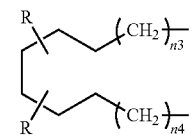

(4)

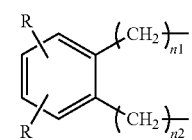

(5)

wherein $n^1$ and $n^2$ each represent a number of 5 to 30, and may be identical to or different from each other; $n^3$ and $n^4$ each represent a number of 4 to 24, and may be identical to or different from each other; R independently represents a hydrogen atom, or a linear or branched alkyl or alkenyl group having 4 to 40 carbon atoms.

[6]

A method for producing the bismaleimide compound according to any one of [1] to [5], comprising:

a step A of synthesizing an amic acid with an acid anhydride and an alicyclic diamine, and then performing cyclodehydration;

a step B subsequent to the step A, which is a step of synthesizing an amic acid with a reactant obtained in the step A and a diamine, and then performing cyclodehydration; and a step C subsequent to the step B, which is a step of synthesizing a maleamic acid with a reactant obtained in the step B and a maleic anhydride, and then performing cyclodehydration to block molecular chain ends, wherein the acid anhydride is represented by the following formula (6):

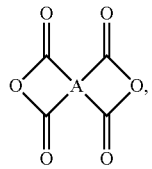   (6)

the alicyclic diamine is represented by the following formula (7):

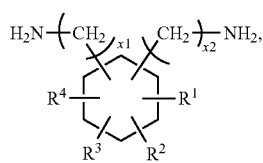   (7)

the diamine is represented by the following formula (8):

   (8), and wherein in the formula (6), A represents a tetravalent organic group having a cyclic structure; in the formula (7), each of $R^1$, $R^2$, $R^3$ and $R^4$ independently represents a hydrogen atom or an alkyl group having 1 to 5 carbon atoms, each of x1 and x2 represents a number of 0 to 4; in the formula (8), B represents a divalent hydrocarbon group having 6 to 200 carbon atoms.

[7]

A method for producing the bismaleimide compound according to any one of [1] to [5], comprising:

a step A' of synthesizing an amic acid with an acid anhydride and a diamine, and then performing cyclodehydration;

a step B' subsequent to the step A', which is a step of synthesizing an amic acid with a reactant obtained in the step A' and an alicyclic diamine, and then performing cyclodehydration; and a step C' subsequent to the step B', which is a step of synthesizing a maleamic acid with a reactant obtained in the step B' and a maleic anhydride, and then performing cyclodehydration to block molecular chain ends, wherein the acid anhydride is represented by the following formula (6):

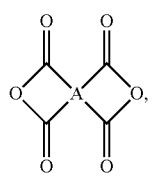   (6)

the diamine is represented by the following formula (8):

   (8), the alicyclic diamine is represented by the following formula (7):

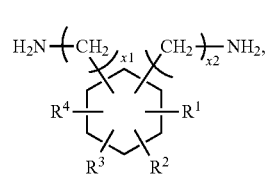   (7)

and wherein in the formula (6), A represents a tetravalent organic group having a cyclic structure; in the formula (8), B represents a divalent hydrocarbon group having 6 to 200 carbon atoms; in the formula (7), each of $R^1$, $R^2$, $R^3$ and $R^4$ independently represents a hydrogen atom or an alkyl group having 1 to 5 carbon atoms, each of x1 and x2 represents a number of 0 to 4.

Since the bismaleimide compound of the present invention, particularly the alicyclic backbone-containing bismaleimide compound is superior in compatibility with resins having different structures, it can be readily used in combination with other resins and easily elicit higher performances via mutual performance compensation. Further, using the bismaleimide compound of the present invention, particularly the alicyclic backbone-containing bismaleimide compound, there can be provided a bismaleimide resin composition exhibiting a low level of variations in curability and property when molded into the shape of a film or substrate, and yielding a cured product having a high glass-transition point (Tg).

DETAILED DESCRIPTION OF THE INVENTION

Figure 1:
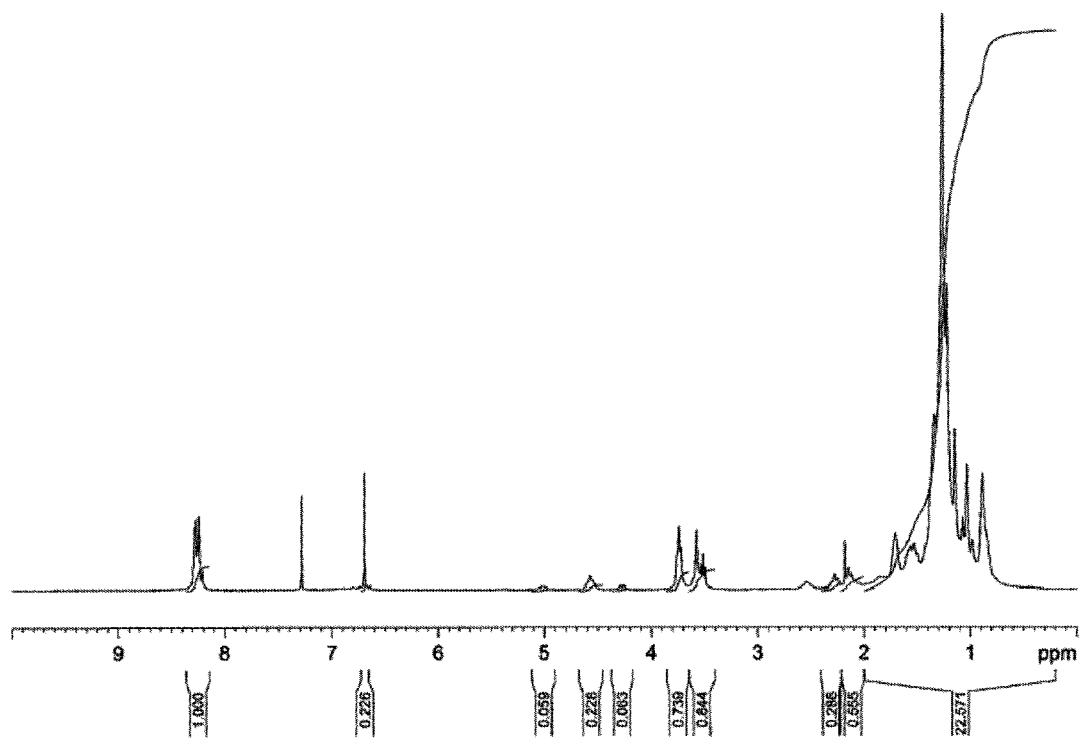
FIG. 1 is a $^1$H-NMR spectrum of a bismaleimide compound synthesized in a synthetic example 1.

The present invention is described in detail hereunder.

A bismaleimide compound of the present invention is represented by the following formula (1):

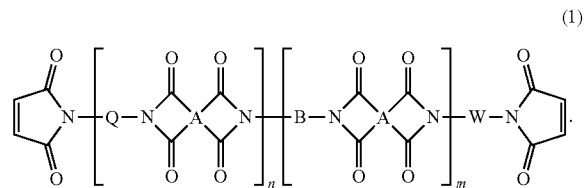   (1)

In the above formula (1), A independently represents a tetravalent organic group having a cyclic structure, B independently represents a divalent hydrocarbon group having not less than six carbon atoms, Q independently represents a cyclohexane backbone-containing divalent alicyclic hydrocarbon group having 6 to 60 carbon atoms, W represents B or Q, n represents 1 to 100, and m represents 0 to 100. Repeating units identified by n and m are present in any order; a bonding pattern of each of these repeating units n and m may be alternate, block or random. Particularly, the divalent alicyclic hydrocarbon group represented by Q is independently represented by the following formula (2):

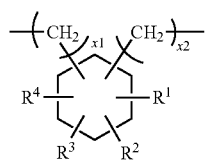
(2)

wherein each of $R^1$, $R^2$, $R^3$ and $R^4$ independently represents a hydrogen atom or an alkyl group having 1 to 5 carbon atoms; each of x1 and x2 represents a number of 0 to 4.

Here, in the formula (1), A independently represents a tetravalent organic group having a cyclic structure, and it is preferred that A represent any one of the tetravalent organic groups represented by the following structural formulae.

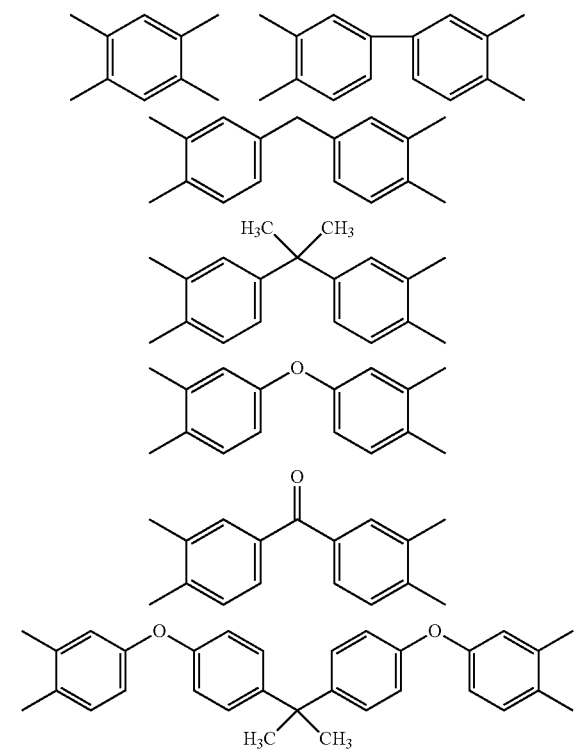

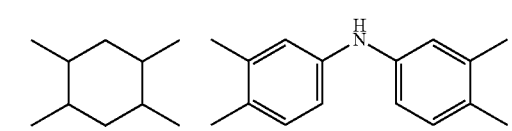

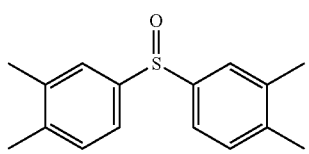

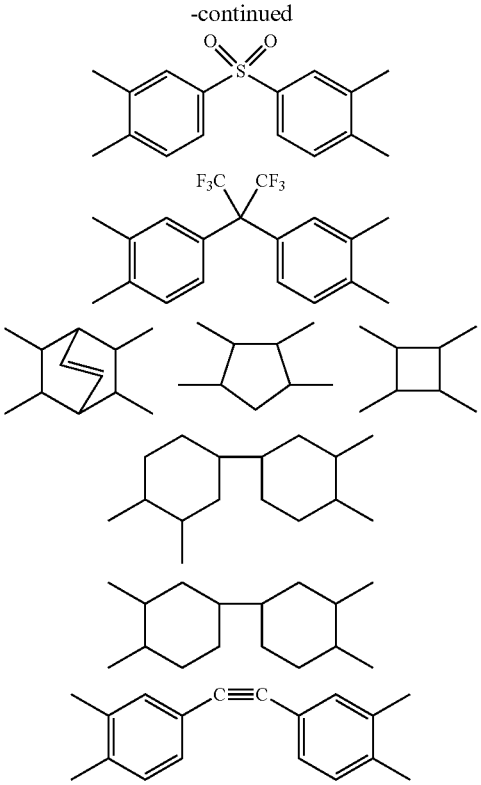

wherein bonds in the above structural formulae that are yet unbonded to substituent groups are to be bonded to carbonyl carbons forming cyclic imide structures in the general formula (1).

Further, in the formula (1), B independently represents a divalent hydrocarbon group having 6 to 200, preferably 8 to 100, more preferably 10 to 50 carbon atoms. Here, it is preferred that B be a branched divalent hydrocarbon group with at least one hydrogen atom therein being substituted by an alkyl group or alkenyl group having 6 to 200, preferably 8 to 100, more preferably 10 to 50 carbon atoms. Such branched divalent hydrocarbon group may be either a saturated aliphatic hydrocarbon group or an unsaturated hydrocarbon group, and an alicyclic structure or aromatic ring structure may be present midway through the molecular chain. Specific examples of the branched divalent hydrocarbon group include a hydrocarbon group derived from a dual-end diamine called dimer diamine. Particularly, dimer diamine refers to a compound derived from a dimer of an unsaturated aliphatic acid such as oleic acid.

Specific examples of the divalent hydrocarbon group include at least one of the divalent hydrocarbon groups represented by the following structural formulae (3-1) to (5).

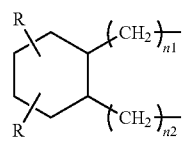
(3-1)

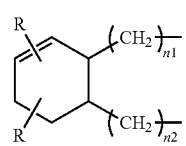 (3-2)

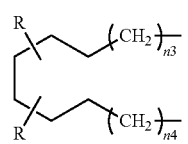 (4)

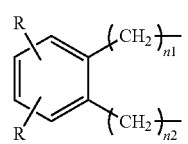 (5)

Here, each of $n^1$ and $n^2$ represents a number of 5 to 30, preferably 5 to 15, more preferably 6 to 10; $n^1$ and $n^2$ may be identical to or different from each other. Further, each of $n^3$ and $n^4$ represents a number of 4 to 24, preferably 4 to 12, more preferably 5 to 10; $n^3$ and $n^4$ may be identical to or different from each other. Furthermore, R independently represents a hydrogen atom, or a linear or branched alkyl or alkenyl group having 4 to 40, preferably 5 to 20, more preferably 6 to 15 carbon atoms. Specific examples of R include a hydrogen atom; a butyl group, a pentyl group, a hexyl group, a heptyl group, an octyl group, a nonyl group, a decyl group, an undecyl group, a lauryl group, a stearyl group and structural isomers thereof.

Specific examples of the formulae (3-1) to (5) include the following structures.

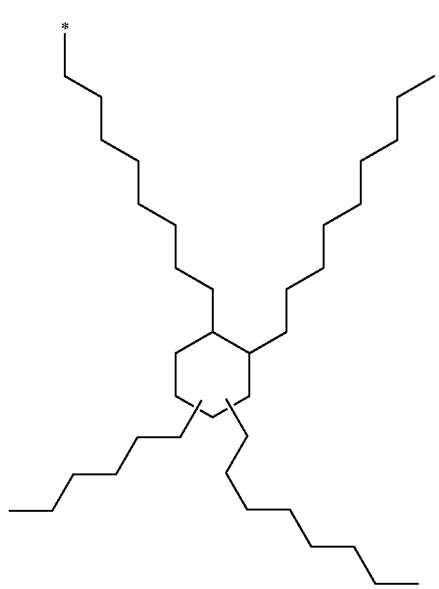

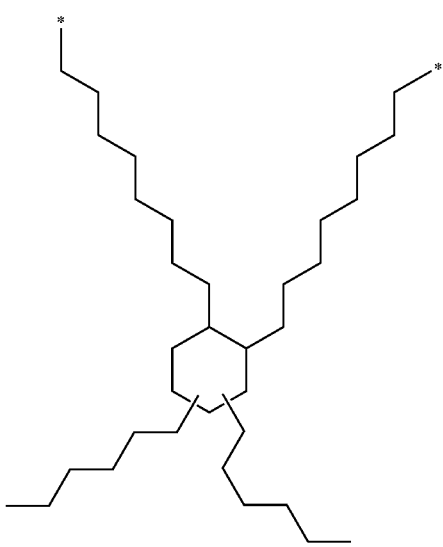

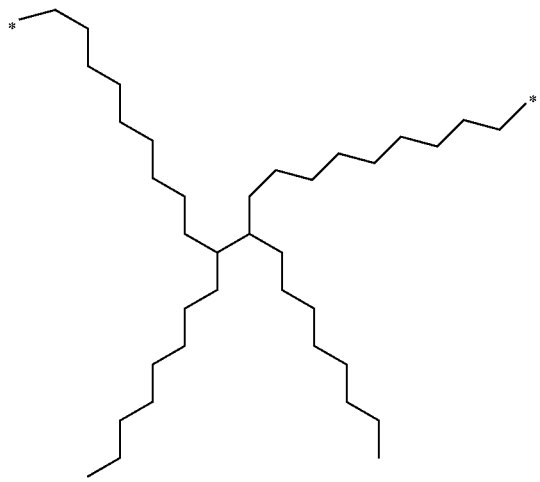

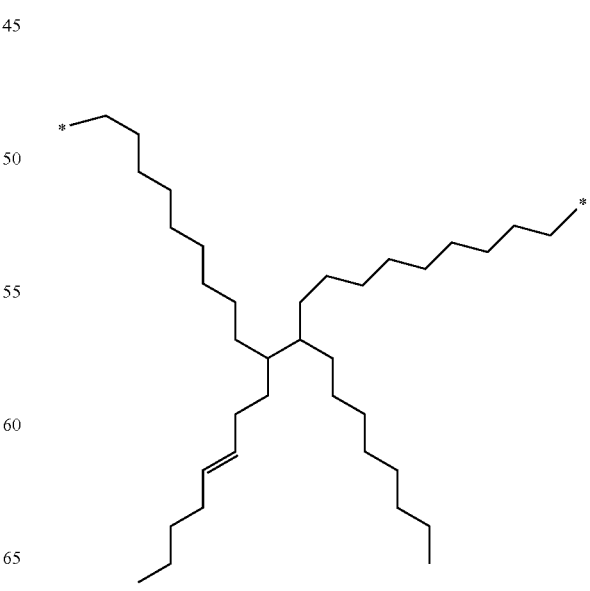

-continued

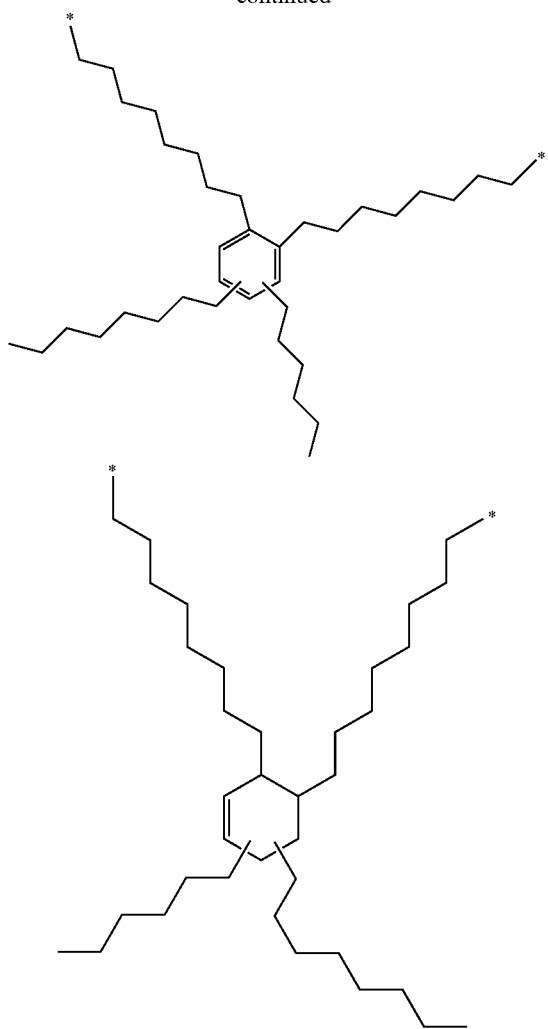

Further, in the formula (1), Q independently represents a cyclohexane backbone-containing divalent alicyclic hydrocarbon group having 6 to 60, preferably 8 to 30, more preferably 10 to 20 carbon atoms. Here, Q is independently expressed by the following formula (2):

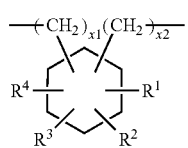
(2)

wherein each of $R^1$, $R^2$, $R^3$ and $R^4$ independently represents a hydrogen atom or an alkyl group having 1 to 5 carbon atoms; each of x1 and x2 represents a number of 0 to 4.

Here, specific examples of $R^1$, $R^2$, $R^3$ and $R^4$ include a hydrogen atom, a methyl group, an ethyl group, an n-propyl group, an isopropyl group, an n-butyl group, an isobutyl group and a t-butyl group. Among these examples, a hydrogen atom and a methyl group are preferred. Particularly, $R^1$, $R^2$, $R^3$ and $R^4$ may be identical to or different from another.

Further, each of x1 and x2 represents a number of 0 to 4, preferably a number of 0 to 2. Particularly, x1 and x2 may be identical to or different from each other.

Further, specific examples of Q in the formula (1) include those having the following structures.

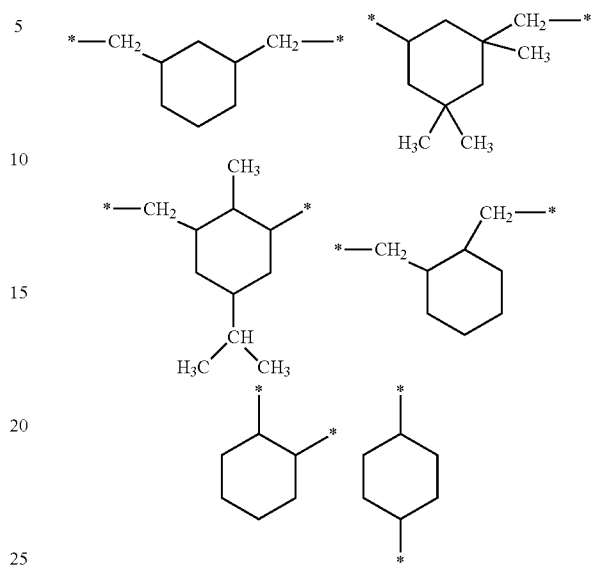

In the formula (1), W represents B or Q. Whether W takes the structural unit of either B or Q is determined by a difference(s) in a later-described production method.

Further, in the formula (1), n represents 1 to 100, preferably 1 to 50, more preferably 1 to 40. Furthermore, m represents 0 to 100, preferably 1 to 50, more preferably 1 to 40.

There are no particular restrictions on a number average molecular weight (Mn) of the bismaleimide compound of the present invention; it is preferred that the bismaleimide compound of the present invention have a number average molecular weight of 3,000 to 50,000, more preferably 3,500 to 30,000, even more preferably 4,000 to 20,000. If the number average molecular weight thereof is within these ranges, a resin composition containing the bismaleimide compound of the present invention will not exhibit an excessively high viscosity, and a cured product of such resin composition shall exhibit a high hardness.

Here, the term "number average molecular weight (Mn)" referred to in this specification means a number average molecular weight measured by GPC under the following conditions, using polystyrene as a reference substance.

[GPC Measurement Condition]
Developing solvent: tetrahydrofuran
Flow rate: 0.6 mL/min
Column: TSK Guardcolumn Super H-L
TSKgel Super H4000 (6.0 mmI.D.×15 cm×1)
TSKgel Super H3000 (6.0 mmI.D.×15 cm×1)
TSKgel Super H2000 (6.0 mmI.D.×15 cm×2)
(all by TOSOH CORPORATION)
Column temperature: 40° C.
Sample injection volume: 20 μL (Sample concentration: 0.5% by mass-tetrahydrofuran solution)
Detector: differential refractometer (RI)

There are no restrictions on an order in which units identified by n and m are repeated; a bonding pattern of each of these units n and m may be alternate, block or random. Here, block bonding is preferred.

Method for Producing Bismaleimide Compound

There are no particular restrictions on a method for producing the bismaleimide compound of the present invention. The compound may, for example, be efficiently produced by any one of the two methods shown below.

Production Method 1

A first method for producing the bismaleimide compound includes a step A of synthesizing an amic acid with an acid anhydride and an alicyclic diamine, and then performing cyclodehydration; a step B subsequent to the step A, which is a step of synthesizing an amic acid with the reactant obtained in the step A and a diamine, and then performing cyclodehydration; and a step C subsequent to the step B, which is a step of synthesizing a maleamic acid with the reactant obtained in the step B and a maleic anhydride, and then performing cyclodehydration to block molecular chain ends with maleimide groups.

The acid anhydride used in the step A is represented by the following formula (6):

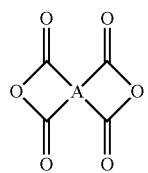

(6)

wherein A is defined as above in the formula (1).

The alicyclic diamine used in the step A is represented by the following formula (7):

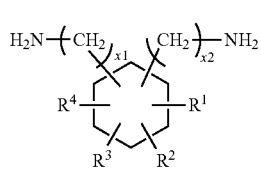

(7)

wherein $R^1$, $R^2$, $R^3$, $R^4$, x1 and x2 are defined as above in the formula (1).

The diamine used in the step B is represented by the following formula (8):

$H_2N-B-NH_2$ (8)

wherein B is defined as above in the formula (1).

Production Method 2

A second method for producing the bismaleimide compound includes a step A' of synthesizing an amic acid with the acid anhydride represented by the formula (6) and the diamine represented by the formula (8), and then performing cyclodehydration; a step B' subsequent to the step A', which is a step of synthesizing an amic acid with the reactant obtained in the step A' and the alicyclic diamine represented by the formula (7), and then performing cyclodehydration; and a step C' subsequent to the step B', which is a step of synthesizing a maleamic acid with the reactant obtained in the step B' and a maleic anhydride, and then performing cyclodehydration to block molecular chain ends.

The two production methods have now been described. As a basic pattern, the bismaleimide compound can be obtained by the step A (or step A') of synthesizing an amic acid with a tetracarboxylic dianhydride and a diamine, and then performing cyclodehydration; the step B (or step B') subsequent to the step A (or step A'), which is a step of synthesizing an amic acid by adding a diamine other than that employed in the previous step A (or step A'), and then further performing cyclodehydration; and then the step C (or step C') subsequent to the step B (or step B'), which is a step of reacting a maleic anhydride to synthesize a maleamic acid, and then finally performing cyclodehydration to block molecular chain ends with maleimide groups. The above two production methods mainly differ from each other only in the order in which the different types of diamines are added.

In the above two production methods, the steps can be grouped into two categories which are the synthesis reaction of an amic acid or maleamic acid; and the cyclodehydration reaction. These reactions are described in detail hereunder.

In the step A (or step A'), an amic acid is at first synthesized by reacting a particular tetracarboxylic dianhydride with a particular diamine. This reaction usually proceeds in an organic solvent (e.g. non-polar solvent or high-boiling aprotic polar solvent) and at a temperature of room temperature (25° C.) to 100° C.

Next, the cyclodehydration reaction of the amic acid is performed in a way such that after reacting the amic acid at a temperature of 90 to 120° C., the cyclodehydration reaction is then caused to proceed while removing from the system a water produced as a by-product due to a condensation reaction. An organic solvent (e.g. non-polar solvent, high-boiling aprotic polar solvent) and/or an acid catalyst may also be added to promote the cyclodehydration reaction.

Examples of the organic solvent include toluene, xylene, anisole, biphenyl, naphthalene, N,N-dimethylformamide (DMF) and dimethylsulfoxide (DMSO). Any one of these organic solvents may be used alone, or two or more of them may be used in combination. Further, examples of the acid catalyst include sulfuric acid, methanesulfonic acid and trifluoromethanesulfonic acid. Any one of these acid catalysts may be used alone, or two or more of them may be used in combination.

A molar ratio between the tetracarboxylic dianhydride and the diamine is preferably tetracarboxylic dianhydride/diamine=1.01 to 1.50/1.0, more preferably tetracarboxylic dianhydride/diamine=1.01 to 1.35/1.0. By combining the tetracarboxylic dianhydride and the diamine at this ratio, there can be synthesized, as a result, a copolymer having an imide group at both ends.

In the step B (or step B'), an amic acid is at first synthesized by reacting the copolymer obtained in the step A (or step A') with a particular diamine, the copolymer being that having an imide group at both ends. This reaction also usually proceeds in an organic solvent (e.g. non-polar solvent or high-boiling aprotic polar solvent) and at a temperature of room temperature (25° C.) to 100° C.

Likewise, the subsequent cyclodehydration reaction of the amic acid is performed in a way such that after reacting the amic acid at a temperature of 95 to 120° C., the cyclodehydration reaction is then caused to proceed while removing from the system a water produced as a by-product due to a condensation reaction. An organic solvent (e.g. non-polar solvent, high-boiling aprotic polar solvent) and/or an acid catalyst may also be added to promote the cyclodehydration reaction.

Examples of the organic solvent include toluene, xylene, anisole, biphenyl, naphthalene, N,N-dimethylformamide (DMF) and dimethylsulfoxide (DMSO). Any one of these organic solvents may be used alone, or two or more of them may be used in combination. Further, examples of the acid catalyst include sulfuric acid, methanesulfonic acid and trifluoromethanesulfonic acid. Any one of these acid catalysts may be used alone, or two or more of them may be used in combination.

A molar ratio between the copolymer having an imide group at both ends and the diamine is preferably 1.0:1.6 to 2.5, more preferably 1.0:1.8 to 2.2.

In the step C (or step C'), a maleamic acid is synthesized by reacting, at a temperature of room temperature (25° C.) to 100° C., a diamine having an amino group at both ends with a maleic anhydride, the diamine being that obtained in the step B (or B'). Finally, cyclodehydration is performed while removing from the system a water produced at 95 to 120° C. as a by-product, thereby blocking the molecular chain ends with maleimide groups, thus obtaining the target bismaleimide compound. It is preferred that the reaction for blocking the molecular chain ends with maleimide groups be performed at a temperature of not higher than 120° C., because side reactions are less likely to occur, and products with higher molecular weights are less likely to be produced.

With such production method(s), the bismaleimide compound obtained shall have the structure of a block copolymer, thereby homogenizing and improving the compatibility of the resin synthesized.

A molar ratio between the diamine having an amino group at both ends and the maleic anhydride is preferably 1.0:1.6 to 2.5, more preferably 1.0:1.8 to 2.2.

A method for refining the compound of the present invention may be a common method; the compound may, for example, be refined by reprecipitation.

WORKING EXAMPLES

The present invention is described in detail hereunder with reference to working, reference and comparative reference examples. However, the present invention is not limited to the following working examples. In the working, reference and comparative reference examples, the term "room temperature" means 25° C.

Working Example 1 (Production of Bismaleimide Compound, Reaction Formula 1)

Isophoronediamine of 37.25 g (0.219 mol), pyromellitic dianhydride of 76.94 g (0.35 mol) and toluene of 350 g were added to a 2 L glass four-necked flask equipped with a stirrer, a Dean-Stark tube, a cooling condenser and a thermometer, followed by stirring them at 80° C. for three hours to synthesize an amic acid. Next, the temperature was directly raised to 110° C., and stirring was performed for another four hours while distilling away a water produced as a by-product, thereby synthesizing a block copolymer.

Later, 116.88 g (0.219 mol) of Priamine-1075 (by CRODA, a diamine compound expressed by $H_2N-C_{36}H_{70}-NH_2$ (average composition formula) and containing a dimer diamine represented by the following formulae (3') to (5')) was added to the flask containing the block copolymer solution that had been cooled to room temperature, followed by performing stirring at 80° C. for three hours to synthesize an amic acid. Next, the temperature was directly raised to 110° C., and stirring was performed for another four hours while distilling away a water produced as a by-product, thereby synthesizing a dual-end diamine body.

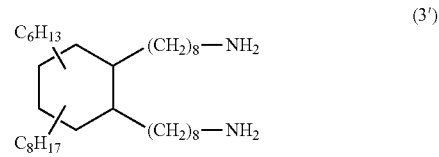

(3')

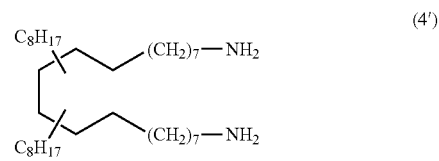

(4')

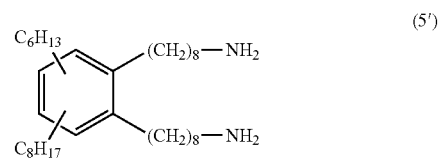

(5')

Figure 2:
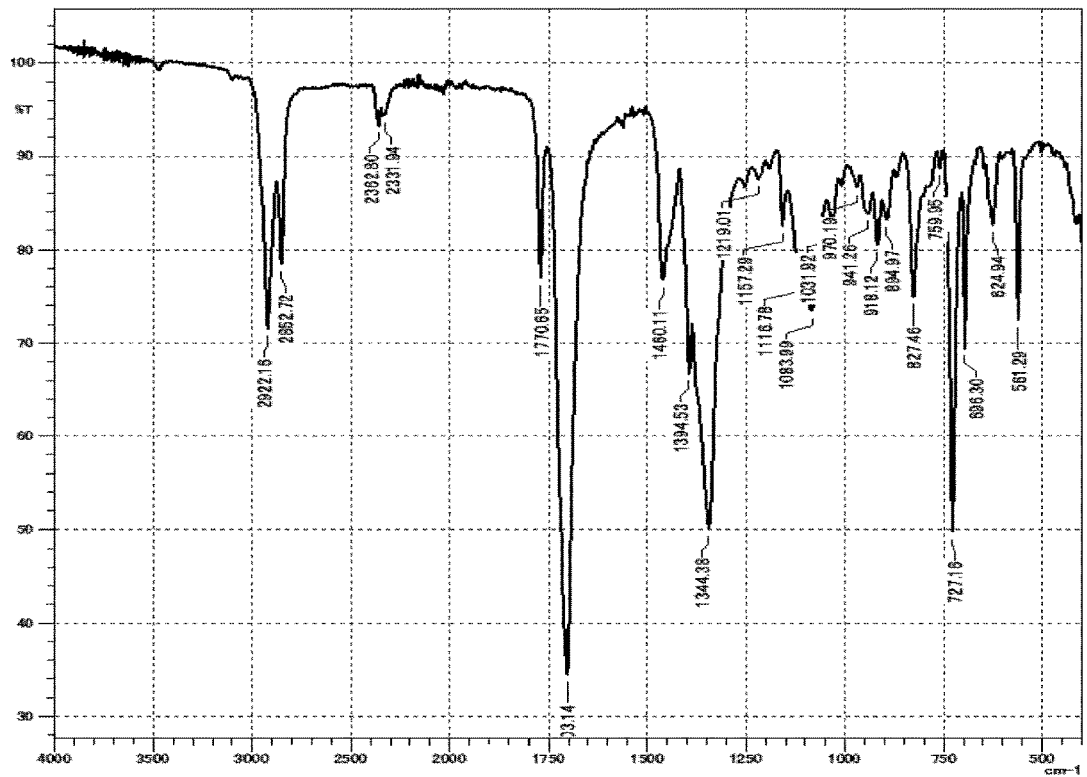
FIG. 2 is an IR spectrum of the bismaleimide compound synthesized in the synthetic example 1.

After cooling the flask containing the dual-end diamine body solution obtained to room temperature, 18.88 g (0.193 mol) of maleic anhydride was added thereto, followed by heating the flask again and performing stirring at 80° C. for three hours to synthesize an amic acid. Next, the temperature was directly raised to 110° C., and stirring was performed for another 15 hours while distilling away a water produced as a by-product, followed by performing washing with 300 g of water five times so as to obtain a varnish of a bismaleimide compound. Later, a reprecipitation step was carried out by delivering the varnish into 3,000 g of isopropyl alcohol (IPA) by drops, followed by removing the solvent and then performing drying so as to obtain a target seal brown solid. Based on a $^1$H-NMR and IR spectra of the product obtained, it was confirmed that the product was a bismaleimide compound 1 (number average molecular weight: 8,000) having a structure represented by a formula (9) in the following reaction formula 1. The $^1$H-NMR spectrum is shown in FIG. 1, and the IR spectrum is shown in FIG. 2.

(Reaction formula 1)

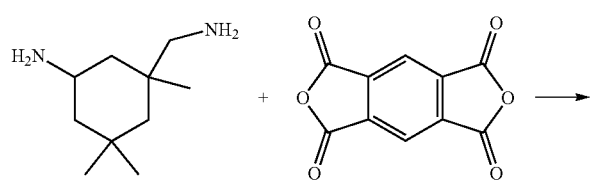

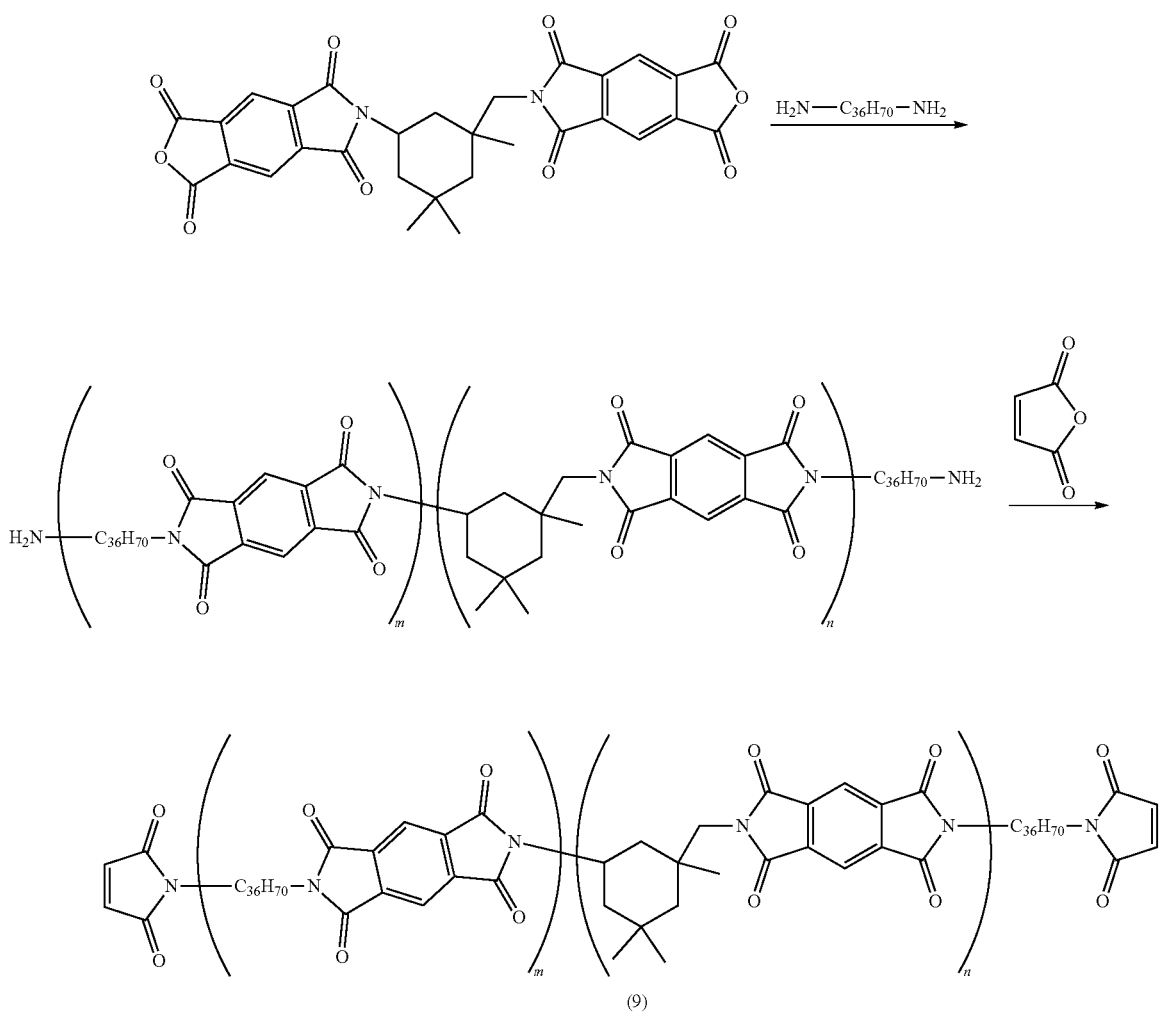

H$_2$N—C$_{36}$H$_{70}$—NH$_2$ represents Priamine-1075
m≈3, n≈1 (both are average values)

$^1$H-NMR (400 MHz, CDCl$_3$) δ 0.80-2.00 (alkyl group, 100H), 2.05-2.25 (—CH$_2$—CH$_2$—CH$_2$—, m, ~6H), 3.47-3.63 (—N—CH$_2$—CH$_2$—, m, 12H), 3.65-3.85 (—N—C H$_2$—CH$_2$—, m, 12H), 4.26 (—CH—CH$_2$—C—, d, 1H), 4.59 (—N—CH—CH$_2$—, t, 4H), 5.05 (—N—CH—CH$_2$—, br, 1H), 7.06-7.14 (derived from aromatic ring, 8H), 6.70 (derived from maleimide, s, 16H), 8.15-8.36 (derived from aromatic ring, m, 4H)

Working Example 2 (Production of Bismaleimide Compound, Reaction Formula 2)

Isophoronediamine of 89.41 g (0.525 mol), pyromellitic dianhydride of 76.94 g (0.35 mol) and toluene of 350 g were added to a 2 L glass four-necked flask equipped with a stirrer, a Dean-Stark tube, a cooling condenser and a thermometer, followed by stirring them at 80° C. for three hours to synthesize an amic acid. Next, the temperature was directly raised to 110° C., and stirring was performed for another four hours while distilling away a water produced as a by-product, thereby synthesizing a block copolymer.

Later, 116.88 g (0.219 mol) of Priamine-1075 (by CRODA, a diamine compound expressed by H$_2$N—C$_{36}$H$_{70}$—NH$_2$ (average composition formula)) was added to the flask containing the block copolymer solution that had been cooled to room temperature, followed by performing stirring at 80° C. for three hours to synthesize an amic acid. Next, the temperature was directly raised to 110° C., and stirring was performed for another four hours while distilling away a water produced as a by-product, thereby synthesizing a dual-end diamine body.

After cooling the flask containing the dual-end diamine body solution obtained to room temperature, 18.88 g (0.193 mol) of maleic anhydride was added thereto, followed by heating the flask again and performing stirring at 80° C. for three hours to synthesize an amic acid. Next, the temperature was directly raised to 110° C., and stirring was performed for another 15 hours while distilling away a water produced as a by-product, followed by performing washing with 300 g of water five times so as to obtain a varnish of a bismaleimide compound. Later, a reprecipitation step was carried out by delivering the varnish into 2,000 g of IPA by drops, followed by removing the solvent and then performing drying so as to obtain a target seal brown solid. Based on a $^1$H-NMR and IR spectra of the product obtained, it was confirmed that the product was a bismaleimide compound 2 (number average molecular weight: 8,500) having a structure represented by a formula (10) in the following reaction formula 2.

(Reaction formula 2)

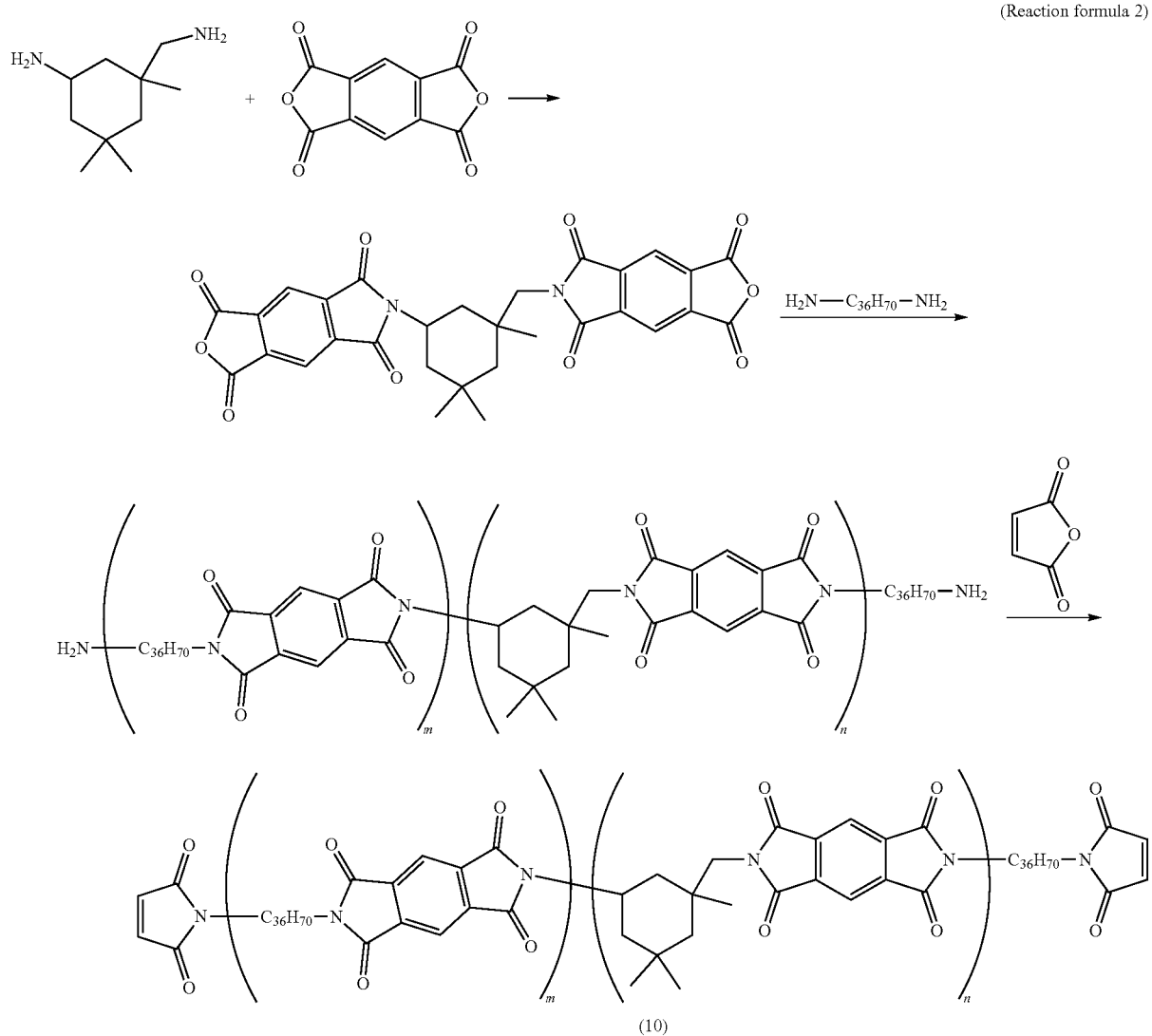

H$_2$N—C$_{36}$H$_{70}$—NH$_2$ represents Priamine-1075
m≈5, n≈1 (both are average values)

Working Example 3 (Production of Bismaleimide Compound, Reaction Formula 3)

1,3-bisaminomethylcyclohexane of 31.13 g (0.219 mol), pyromellitic dianhydride of 76.94 g (0.35 mol) and toluene of 350 g were added to a 2 L glass four-necked flask equipped with a stirrer, a Dean-Stark tube, a cooling condenser and a thermometer, followed by stirring them at 80° C. for three hours to synthesize an amic acid. Next, the temperature was directly raised to 110° C., and stirring was performed for another four hours while distilling away a water produced as a by-product, thereby synthesizing a block copolymer.

Later, 116.88 g (0.219 mol) of Priamine-1075 (by CRODA, a diamine compound expressed by H$_2$N—C$_{36}$H$_{70}$—NH$_2$ (average composition formula)) was added to the flask containing the block copolymer solution that had been cooled to room temperature, followed by performing stirring at 80° C. for three hours to synthesize an amic acid. Next, the temperature was directly raised to 110° C., and stirring was performed for another four hours while distilling away a water produced as a by-product, thereby synthesizing a dual-end diamine body.

After cooling the flask containing the dual-end diamine body solution obtained to room temperature, 18.88 g (0.193 mol) of maleic anhydride was added thereto, followed by heating the flask again and performing stirring at 80° C. for three hours to synthesize an amic acid. Next, the temperature was directly raised to 110° C., and stirring was performed for another 15 hours while distilling away a water produced as a by-product, followed by performing washing with 300 g of water five times so as to obtain a varnish of a bismaleimide compound. Later, a reprecipitation step was carried out by delivering the varnish into 2,000 g of IPA by drops, followed by removing the solvent and then performing drying so as to obtain a target seal brown solid. Based on a $^1$H-NMR and IR spectra of the product obtained, it was confirmed that the product was a bismaleimide compound 3 (number average molecular weight: 7,600) having a structure represented by a formula (11) in the following reaction formula 3.

(Reaction formula 3)
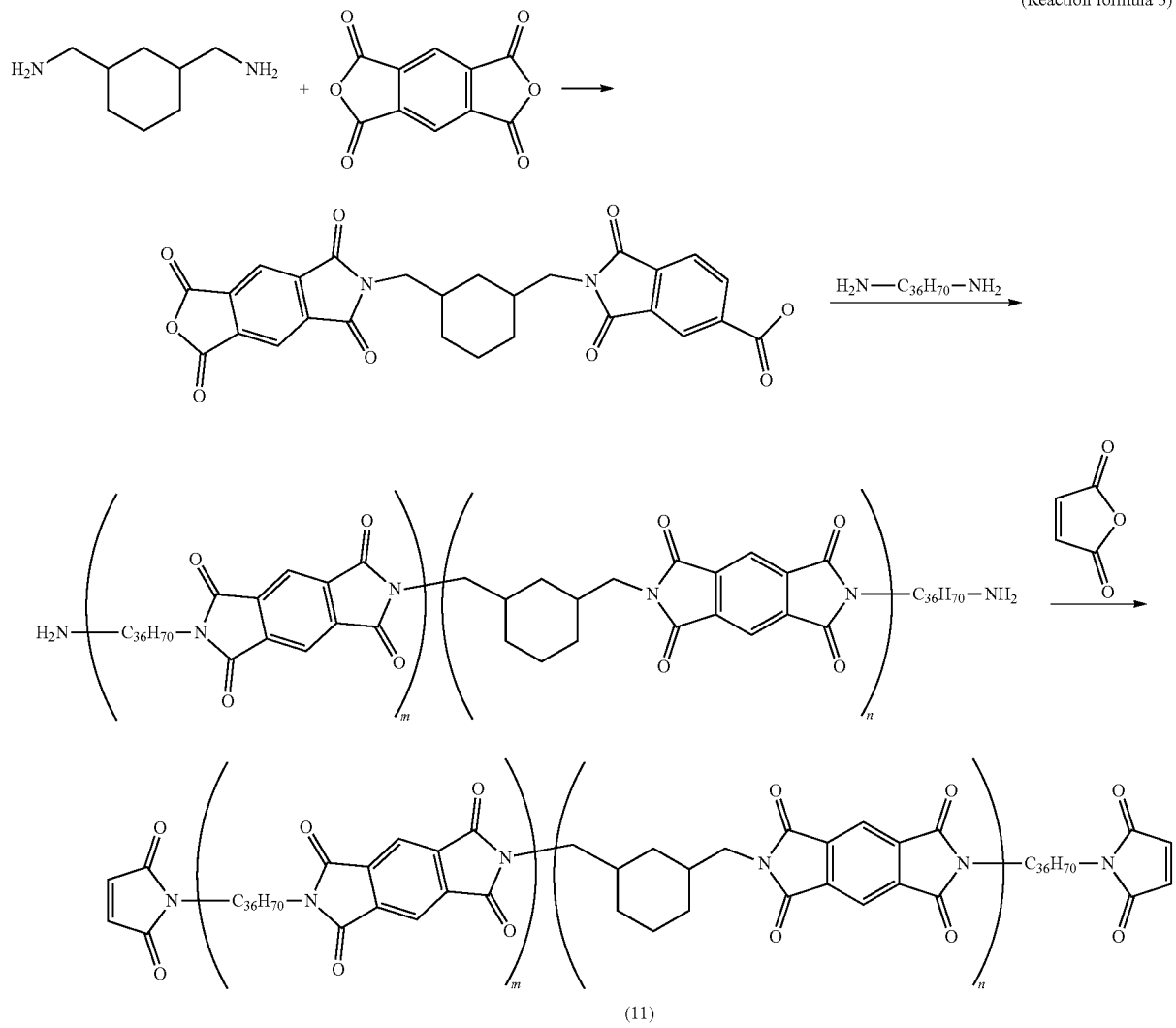
(11)
$H_2N-C_{36}H_{70}-NH_2$ represents Priamine-1075
n≈3, n≈1 (both are average values)
Bismaleimide Compound
  (BMI-1) Linear Alkylene Group-Containing Bismaleimide Compound Represented by the Following Formula (BMI-1500 by Designer Molecules Inc. for Use in Comparative Reference Examples)
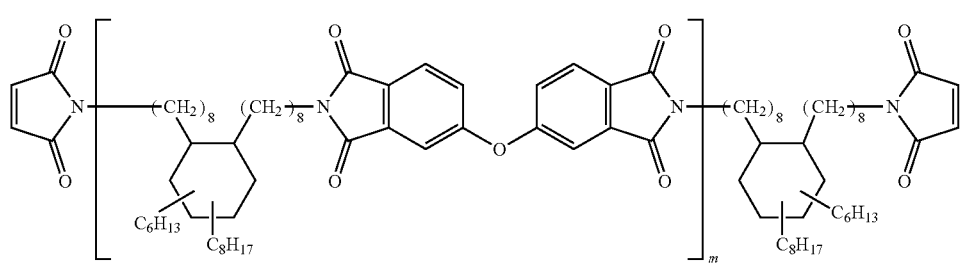
m ≈ 2 (Average Value)

(BMI-2) Linear Alkylene Group-Containing Bismaleimide Compound Represented by the Following Formula (BMI-3000) by Designer Molecules Inc. for Use in Comparative Reference Examples)

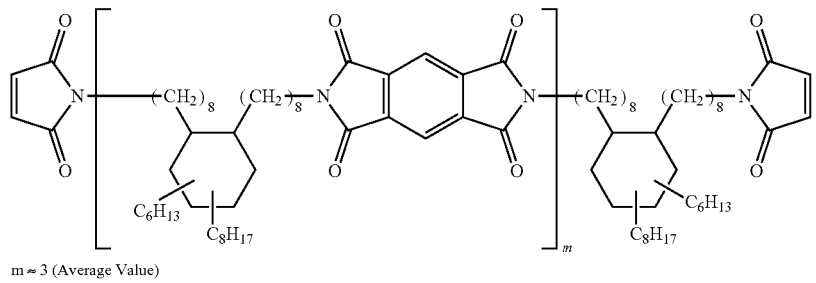

m ≈ 3 (Average Value)

(BMI-3) Linear Alkylene Group-Containing Bismaleimide Compound Represented by the Following Formula (BMI-2500 by Designer Molecules Inc. for Use in Comparative Reference Examples)

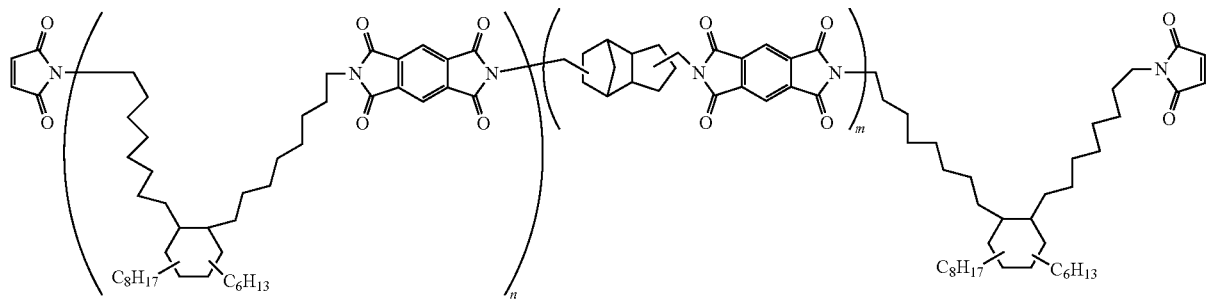

n ≈ 3, m ≈ 3 (Both are average values)

(BMI-4) 4,4'-Diphenylmethanebismaleimide (BMI-1000 by Daiwa Fine Chemicals Co., Ltd. for Use in Comparative Reference Examples)

Reference Examples 1 to 3; Comparative Reference Examples 1 to 4

Each of the bismaleimide compounds 1 to 3 synthesized in the working examples 1 to 3 and the bismaleimide compounds BMI-1 to 4 was taken by an amount of 100 g and combined with 1 g of dicumylperoxide in a metal petri dish, followed by placing the petri dish on a hot plate of 100° C. and performing mixing for 10 min to prepare a bismaleimide resin composition.

Compatibility

Compatibility with PPE Resin

Each bismaleimide resin composition prepared as above was taken by an amount of 20 g and combined with 20 g of a terminal-methacryl-modified polyphenylene ether resin (SA9000-111 by SABIC, molecular weight 4,000) and 40 g of toluene in a 100 mL transparent glass bottle, followed by heating and mixing them at 80° C. for 30 min. Later, the mixture was cooled to room temperature, and an appearance thereof was observed. Evaluation results are shown in Table 1.

Compatibility with BMI-2

Among the bismaleimide resin compositions prepared as above, each of the resin compositions containing the bismaleimide compounds 1 to 3 synthesized in the working examples 1 to 3 and the resin compositions containing BMI-3 and BMI-4 was taken by an amount of 20 g and combined with 20 g of BMI-2 and 40 g of toluene in a 100 mL transparent glass bottle, followed by heating and mixing them at 80° C. for 30 min. Later, the mixture was cooled to room temperature, and an appearance thereof was observed. Evaluation results are shown in Table 1.

Curability

Appearance

Each of the bismaleimide compounds 1 to 3 synthesized in the working examples 1 to 3 and the bismaleimide compounds BMI-1 to 4 was taken by an amount of 50 g and combined with 50 g of the terminal-methacryl-modified polyphenylene ether resin (SA9000-111) and 1 g of dicumylperoxide in a metal petri dish, followed by placing the petri dish on a hot plate of 100° C. and performing mixing for 10 min to prepare a bismaleimide resin composition for curability evaluation. A vacuum press machine (by Nikko-Materials Co., Ltd.) was then used to mold the bismaleimide resin composition for curability evaluation thus prepared into the shape of a film having a thickness of 200 μm at 150° C. and in 5 min, followed by performing post curing at 180° C. for two hours to produce a film-shaped sample. An appearance of the sample was visually evaluated, and evaluation results are shown in Table 1.

DSC

Further, DSC of the bismaleimide resin composition for curability evaluation was measured under the following conditions, and numbers of exothermic peaks are shown in Table 1.

DSC Measurement Condition

Measurement device: DSC 3+ by METTLER TOLEDO.
Sample weight: 10 mg (weighed using aluminum cell)
Temperature rising rate: 10° C./min Atmosphere: Air
Temperature range: 25 to 300° C.

Dielectric Property (Relative Permittivity, Dielectric Tangent)

A vacuum press machine (by Nikko-Materials Co., Ltd.) was used to mold each bismaleimide resin composition prepared as above into the shape of a film having a thickness of 200 μm at 150° C. and in 5 min, followed by performing post curing at 180° C. for two hours to produce a film-shaped sample for dielectric property evaluation. Later, a network analyzer (E5063-2D5 by Keysight Technologies) and a stripline (by KEYCOM Corp.) were connected to this sample to measure a relative permittivity and dielectric tangent of the film at a frequency of 10 GHz. Measurement results are shown in Table 1.

Glass-Transition Temperature (Tg)

DMA-800 (by TA Instruments) was used to measure a glass-transition temperature of the film-shaped sample for dielectric property evaluation produced as above. Measurement results are shown in Table 1.

TABLE 1

| Property evaluation | | | Reference example 1 | Reference example 2 | Reference example 3 | Comparative reference example 1 | Comparative reference example 2 | Comparative reference example 3 | Comparative reference example 4 |
|---|---|---|---|---|---|---|---|---|---|
| | Bismaleimide compound | | Bismaleimide compound 1 | Bismaleimide compound 2 | Bismaleimide compound 3 | BMI-1 | BMI-2 | BMI-3 | BMI-4 |
| | Compatibility | PPE | Compatible Transparent | Compatible Transparent | Compatible Transparent | Compatible Transparent | Separated | Separated | Turbid Non-transparent |
| | | BMI-2 | Compatible Transparent | Compatible Transparent | Compatible Transparent | — | — | Separated | Separated |
| | Curability | Appearance | Transparent | Transparent | Transparent | Transparent | Separated Mottled pattern confirmed | Separated Mottled pattern confirmed | Turbid Non-transparent |
| | | DSC | 1 | 1 | 1 | 1 | 2 | 2 | 2 |
| Dielectric property (10 GHz) | Relative permittivity | | 2.4 | 2.6 | 2.5 | 2.4 | 2.3 | 2.5 | 3.1 |
| | Dielectric tangent | | 0.002 | 0.006 | 0.003 | 0.002 | 0.002 | 0.003 | 0.010 |
| Glass-transition temperature (DMA)[° C.] | | | 145 | 163 | 139 | 15 | 50 | 140 | 210 |

The bismaleimide resin compositions in the reference examples 1 to 3 exhibited glass-transition point (Tg) higher than those of the bismaleimide resin compositions in the comparative reference examples 1 to 4. Further, it was confirmed that the bismaleimide compounds used in the bismaleimide resin compositions of the reference examples 1 to 3 had a favorable compatibility with other resins.

INDUSTRIAL APPLICABILITY

Using the bismaleimide compound of the present invention, there can be provided a bismaleimide resin composition exhibiting a low level of variations in curability and property when molded into the shape of a film or substrate, and yielding a cured product having a high glass-transition point (Tg). Further, since the bismaleimide compound of the present invention is superior in compatibility with resins having different structures, it can be readily used in combination with other resins and easily elicit higher performances via mutual performance compensation when added to a bismaleimide resin composition. Specifically, the bismaleimide compound of the present invention is suitable for use in, for example, a multilayered printed-wiring board used in high-frequency electronic devices inevitably requiring insulating materials with excellent dielectric properties.

What is claimed is:

1. A bismaleimide compound represented by the following formula (1):

$$\text{(1)}$$

wherein A independently represents a tetravalent organic group having a cyclic structure, B independently represents a divalent hydrocarbon group having 6 to 200 carbon atoms, Q independently represents a cyclohexane backbone-containing divalent alicyclic hydrocarbon group having 6 to 60 carbon atoms, W represents B or Q, n represents 1 to 100, m represents 0 to 100, repeating units identified by n and m are present in any order, a bonding pattern of each of the repeating units n and m may be alternate, block or random, and wherein Q is independently represented by the following formula (2):

$$\text{(2)}$$

wherein each of $R^1$, $R^2$, $R^3$ and $R^4$ independently represents a hydrogen atom or an alkyl group having 1 to 5 carbon atoms, each of x1 and x2 represents a number of 0 to 4.

2. The bismaleimide compound according to claim 1, wherein A in the formula (1) represents any one of the tetravalent organic groups represented by the following structural formulae:

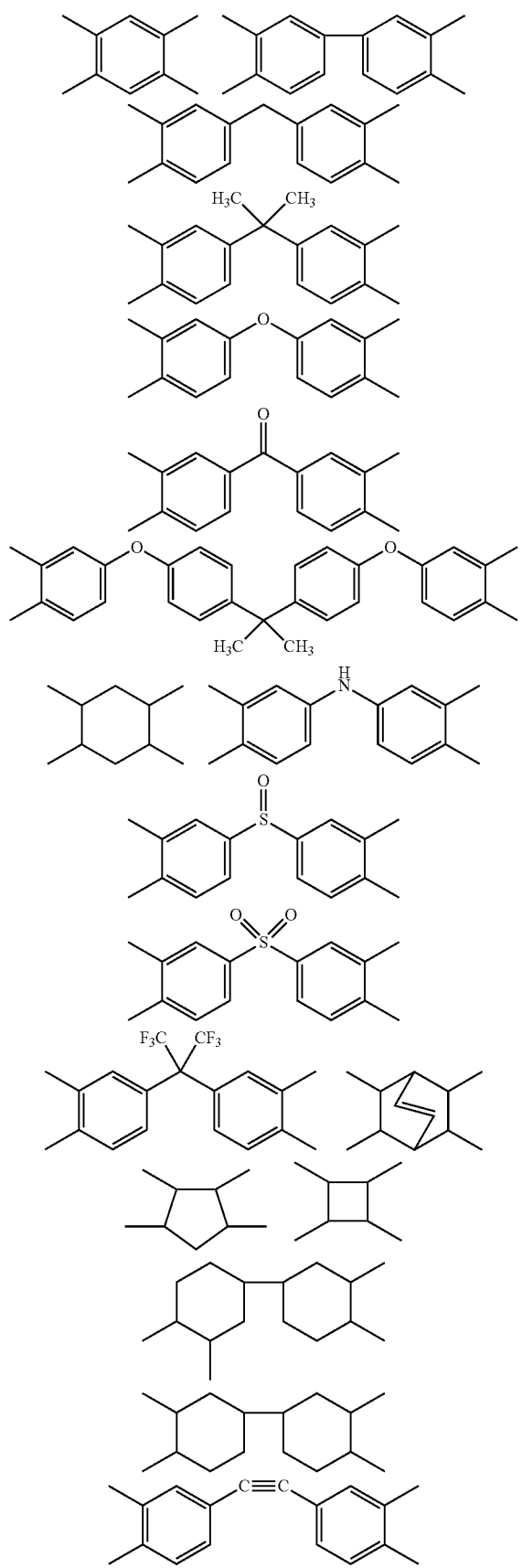

wherein bonds in the above structural formulae that are yet unbonded to substituent groups are to be bonded to carbonyl carbons forming cyclic imide structures in the formula (1).

3. The bismaleimide compound according to claim 1, wherein the bismaleimide compound represented by the formula (1) has a number average molecular weight of 3,000 to 50,000.

4. The bismaleimide compound according to claim 1, wherein the bonding pattern of each of the repeating units identified by n and m is block in the bismaleimide compound represented by the formula (1).

5. The bismaleimide compound according to claim 1, wherein B in the formula (1) comprises at least one of the divalent hydrocarbon groups represented by the following structural formulae (3-1) to (5):

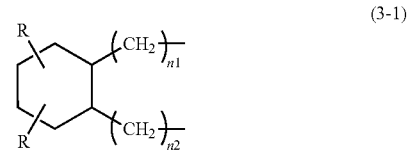 (3-1)

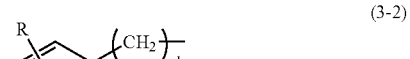 (3-2)

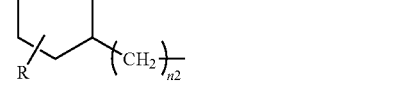 (4)

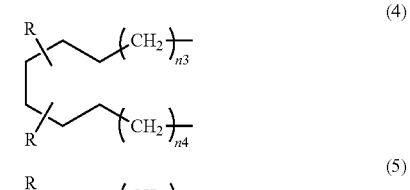 (5)

wherein $n^1$ and $n^2$ each represent a number of 5 to 30, and may be identical to or different from each other; $n^3$ and $n^4$ each represent a number of 4 to 24, and may be identical to or different from each other; R independently represents a hydrogen atom, or a linear or branched alkyl or alkenyl group having 4 to 40 carbon atoms.

6. A method for producing the bismaleimide compound according to claim 1, comprising:

a step A of synthesizing an amic acid with an acid anhydride and an alicyclic diamine, and then performing cyclodehydration;

a step B subsequent to the step A, which is a step of synthesizing an amic acid with a reactant obtained in the step A and a diamine, and then performing cyclodehydration; and a step C subsequent to the step B, which is a step of synthesizing a maleamic acid with a reactant obtained in the step B and a maleic anhydride, and then performing cyclodehydration to block molecular chain ends, wherein the acid anhydride is represented by the following formula (6):

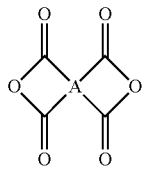
(6)

the alicyclic diamine is represented by the following formula (7):

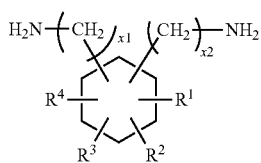
(7)

the diamine is represented by the following formula (8):

H$_2$N—B—NH$_2$ (8), and wherein in the formula (6), A represents a tetravalent organic group having a cyclic structure; in the formula (7), each of R$^1$, R$^2$, R$^3$ and R$^4$ independently represents a hydrogen atom or an alkyl group having 1 to 5 carbon atoms, each of x1 and x2 represents a number of 0 to 4; in the formula (8), B represents a divalent hydrocarbon group having 6 to 200 carbon atoms.

7. A method for producing the bismaleimide compound according to claim 1, comprising:

a step A' of synthesizing an amic acid with an acid anhydride and a diamine, and then performing cyclodehydration;

a step B' subsequent to the step A', which is a step of synthesizing an amic acid with a reactant obtained in the step A' and an alicyclic diamine, and then performing cyclodehydration; and a step C' subsequent to the step B', which is a step of synthesizing a maleamic acid with a reactant obtained in the step B' and a maleic anhydride, and then performing cyclodehydration to block molecular chain ends, wherein the acid anhydride is represented by the following formula (6):

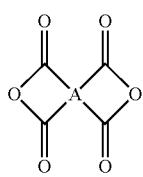
(6)

the diamine is represented by the following formula (8):

H$_2$N—B—NH$_2$ (8), the alicyclic diamine is represented by the following formula (7):

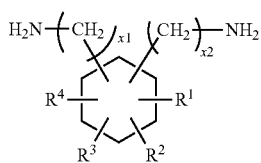
(7)

and wherein in the formula (6), A represents a tetravalent organic group having a cyclic structure; in the formula (8), B represents a divalent hydrocarbon group having 6 to 200 carbon atoms; in the formula (7), each of R$^1$, R$^2$, R$^3$ and R$^4$ independently represents a hydrogen atom or an alkyl group having 1 to 5 carbon atoms, each of x1 and x2 represents a number of 0 to 4.

8. A bismaleimide compound represented by the following formula (1):

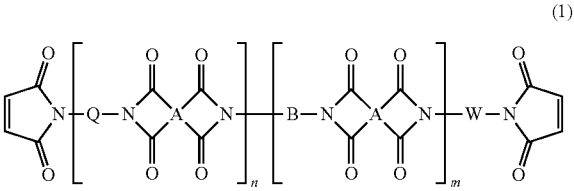
(1)

wherein A is represented by the following structural formula:

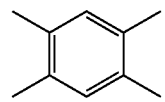

wherein bonds in the above structural formula that are yet unbonded to substituent groups are to be bonded to carbonyl carbons forming cyclic imide structures in the formula (1), B is a divalent hydrocarbon group derived from a dimer diamine, Q is represented by the following structural formula:

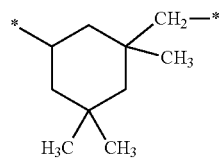

W represents B or Q,
n represents 1 to 100, and
m represents 0 to 100,
wherein repeating units identified by n and m are present in any order, a bonding pattern of each of the repeating units n and m may be alternate, block or random.

9. The bismaleimide compound according to claim 8, wherein the bismaleimide compound represented by the formula (1) has a number average molecular weight of 3,000 to 50,000.

10. The bismaleimide compound according to claim 8, wherein the bonding pattern of each of the repeating units identified by n and m is block in the bismaleimide compound represented by the formula (1).

* * * * *